US012781432B2

(12) United States Patent
Melander et al.

(10) Patent No.: US 12,781,432 B2
(45) Date of Patent: Nov. 3, 2026

(54) REACTOR DISCHARGE

(71) Applicant: VALMET AB, Sundsvall (SE)

(72) Inventors: Olof Melander, Sundsvall (SE); Peter Björklund, Umeå (SE)

(73) Assignee: VALMET AB, Sundsvall (SE)

( * ) Notice: Subject to any disclaimer, the term of this patent is extended or adjusted under 35 U.S.C. 154(b) by 187 days.

(21) Appl. No.: 18/913,068

(22) Filed: Oct. 11, 2024

(65) Prior Publication Data

US 2025/0034806 A1 Jan. 30, 2025

Related U.S. Application Data

(62) Division of application No. 17/252,438, filed as application No. PCT/SE2019/050332 on Apr. 10, 2019, now Pat. No. 12,139,853.

(30) Foreign Application Priority Data

Jun. 26, 2018 (SE) .................................. 1850793-9

(51) Int. Cl.
*D21C 7/08* (2006.01)
*D21B 1/36* (2006.01)
(Continued)

(52) U.S. Cl.
CPC ................ *D21C 7/08* (2013.01); *D21B 1/36* (2013.01); *D21C 1/02* (2013.01); *D21C 1/04* (2013.01);
(Continued)

(58) Field of Classification Search
CPC ... D21C 7/08; D21C 1/02; D21C 7/12; D21B 1/36
See application file for complete search history.

(56) References Cited

U.S. PATENT DOCUMENTS 1,922,313 A 8/1933 Mason
2,616,802 A 11/1952 Kehoe et al.
(Continued)

FOREIGN PATENT DOCUMENTS

CA 2628515 A1 11/2008
CA 2799992 A1 * 12/2011 ........... C12M 45/20
(Continued)

OTHER PUBLICATIONS

Charles E. Wyman, Screw Compression Feeders, Aqueous Pretreatment of Plant Biomass for Biological and Chemical Conversion to Fuels and Chemicals, Wiley, 2013, pp. 434-435.
(Continued)

*Primary Examiner* — Anthony Calandra
(74) *Attorney, Agent, or Firm* — Foley & Lardner LLP

(57) ABSTRACT

A system for processing lignocellulosic materials includes: a pressurization vessel configured to perform hydrothermal treatment of the lignocellulosic materials using saturated or superheated steam; a pressure sealing screw configured to continuously discharge hydrothermally treated lignocellulosic material from the pressurization vessel to a discharge chamber; a control valve configured to add steam to the discharge chamber for pressure control; and a discharge nozzle configured to discharge the lignocellulosic material and steam from the discharge chamber with expansion of steam. The control valve is configured to add the steam to the discharge chamber so as to control a pressure in the discharge chamber to different levels at varying flow rates of the lignocellulosic material and to thereby control a ratio of an amount of steam that escapes through the discharge nozzle to an amount of the lignocellulosic material discharged through the discharge nozzle.

10 Claims, 3 Drawing Sheets

(51) Int. Cl.

| | |
|---|---|
| ***D21C 1/02*** | (2006.01) |
| ***D21C 1/04*** | (2006.01) |
| ***D21C 7/06*** | (2006.01) |
| ***D21C 7/12*** | (2006.01) |

(52) U.S. Cl.
CPC ................. *D21C 7/06* (2013.01); *D21C 7/12* (2013.01); *C12P 2201/00* (2013.01)

(56) References Cited

U.S. PATENT DOCUMENTS

| | | | | |
|---|---|---|---|---|
| 2,882,967 | A | 4/1959 | Surino | |
| 4,506,834 | A | 3/1985 | Ek | |
| 4,881,862 | A | 11/1989 | Dick | |
| 7,303,707 | B2 | 12/2007 | Rafferty et al. | |
| 2009/0221814 | A1 | 9/2009 | Pschorn et al. | |
| 2010/0263814 | A1 | 10/2010 | Dottori et al. | |
| 2012/0041186 | A1 | 2/2012 | Pschorn et al. | |
| 2014/0087432 | A1 * | 3/2014 | Nguyen | D21C 7/10 165/104.11 |
| 2014/0110069 | A1 | 4/2014 | Rawls et al. | |
| 2014/0110509 | A1 | 4/2014 | Rawls et al. | |
| 2015/0233053 | A1 | 8/2015 | Stromberg | |
| 2016/0251682 | A1 | 9/2016 | Dottori et al. | |
| 2019/0136279 | A1 | 5/2019 | Riva et al. | |
| 2019/0241984 | A1 | 8/2019 | Hudebine et al. | |

FOREIGN PATENT DOCUMENTS

| | | | | | |
|---|---|---|---|---|---|
| CN | 104532643 | A | | 4/2015 | |
| CN | 207828156 | U | * | 9/2018 | B01J 3/00 |
| EP | 3156539 | A1 | * | 4/2017 | D21B 1/36 |
| EP | 3 181 219 | A1 | | 6/2017 | |
| GB | 1571700 | A | * | 7/1980 | D21C 7/06 |
| KR | 1020120063955 | A | | 6/2012 | |
| WO | WO-2014/047097 | A1 | | 3/2014 | |
| WO | WO-2014/204519 | A1 | | 12/2014 | |

OTHER PUBLICATIONS

Final Office Action on U.S. Appl. No. 17/252,438 Dtd Apr. 24, 2024.

Muhammad Muzamal et al., Dynamic Simulation of Disintegration of Wood Chips Caused by Impact and Collisions During the Steam Explosion Pretreatment, Wood Science and Technology, Jun. 7, 2016, 18 pages.

Non-Final Office Action on U.S. Appl. No. 17/252,438 Dtd Dec. 21, 2023.

Notice of Allowance on U.S. Appl. No. 17/252,438 Dtd Jul. 18, 2024.

Restriction Requirement on U.S. Appl. No. 17/252,438 Dtd Sep. 29, 2023.

Rydholm, Pulping Processes, 1965, Interscience Publishers, p. 662-667 (Year: 1965).

Supplementary European Search Report, Application No. 19826196, Jan. 11, 2022, 2 pages.

* cited by examiner

REACTOR DISCHARGE

CROSS-REFERENCE TO RELATED APPLICATIONS

This is a divisional of U.S. patent application Ser. No. 17/252,438, filed on Dec. 15, 2020, which is a national stage application of PCT Application No. PCT/SE2019/050332, filed on Apr. 10, 2019, which claims priority to Swedish Patent Application No. 1850793-9, filed on Jun. 26, 2018.

TECHNICAL FIELD

Our invention relates to pre-hydrolysis of lignocellulosic materials e.g. for production of cellulosic sugars or densified pellets or briquettes from lignocellulose materials. Even more specifically, it concerns a method for processing of lignocellulose materials in a reactor under elevated pressure and temperature and an apparatus for continuous discharge of said material and reaction products from the reactor.

BACKGROUND

Methods for hydrothermal treatment of lignocellulose materials, in the following denoted "biomass", with steam explosion discharge are known in the art, for example from U.S. Pat. Nos. 1,922,313 and 7,303,707. The hydrothermal treatment is performed at elevated pressure and temperature by contacting steam with shredded or chipped biomass such that the temperature is increased to a target treatment level. The wet (or dried) biomass is then charged to a pressurized reactor vessel. Steam, which may also be superheated, is added to the reactor for heating of said biomass to saturation temperature by direct condensation. The pressure level of the reactor which may be designed for continuous operation is in the range 5-30 bar and the retention time is in the range 1-20 minutes. During heating of the biomass, mainly hemicellulose compounds are hydrolysed to oligomers and monomers and the molecular weight of lignin is decreased due to breaking of β-aryl ether bonds. Lignocellulose sugar hydrolysis is a pH dependent process; thus, it can be catalysed by adding a mineral acid, for example sulfuric acid, as catalyst to the lignocellulose before or during thermal treatment. The hot and softened biomass is discharged (blown) from the reactor through a blow valve and it cools rapidly when moisture evaporates as pressure drops substantially to ambient. The structure of the lignocellulose breaks down during the discharge and the size of the biomass particles decreases dramatically. The particle disintegration has a positive effect on subsequent process steps, e.g. in enzymatic hydrolysis. Steam exploded biomass is also an excellent substrate for densification to pellets or briquettes of high mechanical durability, bulk density and water resistance. The densified product can be transported as a bulk commodity for final use as sustainable fuel or raw-material to biomass based products and chemicals.

The biomass particles break down during steam explosion due to several mechanisms. One is the "steam explosion" mechanism, by which is meant expansion of steam in the pores and cavities of the biomass, caused by pressure drop during discharge of the material from high pressure to low. The expanding steam swells the pores and cavities and breaks down the rigidity of the material. Another important mechanism for the material disintegration is impact and shear forces when the particles are accelerated to high velocity in the blow valve and hits each other and the walls of the discharge pipe. The importance of the particle velocity for particles' disintegration at steam explosion is demonstrated in a paper given by Muhammad Muzamal, "Dynamic simulation of disintegration of wood chips caused by impact and collisions during the steam explosion pre-treatment"; Wood Science Technology, June 2016; FIG. 9.

Steam explosion is normally accomplished with a blow valve. A mixture of biomass and steam is blown through the valve whereby pressure is rapidly decreasing and the material is accelerated to high velocity by drag forces. The softened biomass is defibrated mechanically as steam and condensate in the pores of the material expands and due to impact and friction caused by the high velocity. The flow in the valve is characterised as a choked (critical) two-phase flow. The steam velocity in the valve is in the order of 200-300 m/s and the blow valve is exposed to very high wear since the steam contains solid material.

Hence, traditionally a steam explosion process is divided in two steps, a first step where the biomass is thermally treated with steam in a pressure vessel and a second step when the softened hot biomass is rapidly and violently discharged from said vessel. The processing conditions for thermal treatment (first step) is set by the duration in the thermal treatment reactor vessel and the temperature (pressure). The second step is the discharging of biomass together with steam through a blow valve from high pressure prevailing in the reactor vessel to ambient pressure. The pressure-drop in the blow valve (second step), at steam explosion discharge, is basically determined by the pressure level of the first step. For example, the up-stream pressure to the discharge device is 15.5 bar(a) if the first step is operated at 200° C. (corresponds to saturated steam at 15.5 bar(a)). Increasing or decreasing the thermal treatment temperature will correspondingly increase or decrease the pressure to the blow valve. This is an unwanted situation in many circumstances since it may be preferred to perform the explosive discharge through the blow valve from a lower pressure than that which corresponds to the thermal treatment temperature.

As said above, the flow through the blow valve comprises a two-phase flow. The steam-to-solids ratio is not controlled but is basically in a complex manner determined by process parameters such as aperture, up-stream pressure, solids particle size distribution, drag and up-stream mixing of the two phases. In parallel with biomass steam, a valuable commodity, is lost through the blow valve. It is preferred to use a small aperture to reduce the loss of steam, but with too small an opening the valve is blocked with biomass and the steam explosion discharge is interrupted. Numerous solutions to resolve such blow valve blockages are proposed already since the early days of steam explosion, for example U.S. Pat. Nos. 1,922,313, 2,882,967, 2,616,802, include solutions to secure the cleanliness of the blow valves, however, at the expense of increased technical complexity and cost.

SUMMARY OF THE INVENTION

An objective of the present invention is to provide a method and apparatus which in an easy and reliable manner overcomes the difficulties discussed above.

This and other objects are achieved by the present invention by means of a method and a system for processing biomass materials.

According to a first aspect of the present invention, systems and methods for simple and improved control of steam usage (steam-to-biomass ratio) at thermal treatment of biomass combined with steam explosion are provided.

According to a second aspect of the present invention, systems and methods where the thermally treatment is decoupled from the steam explosion are provided. Thereby, it is possible to enlarge the temperature operating window of the thermal treatment whilst maintaining control of the particle size reduction due to the steam explosion.

According to a third aspect of the present invention, systems and methods where maintenance costs for wear in a blow valve or discharge nozzle can be significantly reduced are provided, and thereby expenditures for maintenance can be reduced.

The invention is based on the insight that the defibration of the biomass is mainly caused by impact and wear when the mixture of steam violently discharges through an opening from high to low pressure. Steam exercises drag forces on the particles which are accelerated to high velocity in and just after the blow valve. The articles hit each other, the walls of the blow valve and the exhaust conductor (blow pipe) thereby destroying the structure of the by preceding heat treatment softened material. Moisture trapped in the pores and cellular structure of the biomass material starts to evaporate thereby causing pressure forces which will contribute to material defibration. But still, our key observation is that high velocity and mechanical forces play an even more significant role than the pressure forces of expanding steam. According to embodiments of the present invention, there are provided methods and systems for processing biomass in hydrothermal treatment of the material with saturated or superheated steam in a pressurized vessel, comprising a pressure sealing screw for discharging hydrothermally treated lignocellulose material from the pressurized vessel to a discharge chamber, a control valve for adding steam to said discharge chamber for pressure control, and a nozzle for discharging lignocellulose material and steam from discharge chamber.

According to an embodiment of the present invention, a method for treating or processing lignocellulose materials is provided. The method comprises:

- treating lignocellulosic material in a vessel under pressure with saturated or superheated steam;
- continuously discharging lignocellulose material continuously from the vessel to a first chamber using a discharge feeder configured to discharge material at a pressure seal, wherein the discharge feeder is a discharge screw, or a pressure sealing valve, or a pressure sealing discharge feeding wheel.
- adding steam to the first chamber for pressure control; and
- discharging lignocellulose material and steam from the first chamber through a discharge opening such as a discharge valve, or discharge nozzle at simultaneous expansion of steam.

According to an embodiment of the present invention, a method for treating or processing lignocellulose materials is provided. The method comprises:

- providing lignocellulosic material to a pressurized vessel;
- hydrothermally treating lignocellulosic material in said pressurized vessel with saturated or superheated steam;
- discharging hydrothermally treated lignocellulose material continuously from a pressurized vessel to a discharge chamber using a pressure sealing screw;
- adding steam to the discharge chamber for pressure control; and
- discharging lignocellulose material and steam from the discharge chamber through a discharge nozzle at expansion of steam.

According to embodiments of the present invention, the treatment is performed at a pressure of 5-30 bar, and at a temperature of 160-240° C. for a duration of 1-20 minutes followed by continuous discharge of said material from the pressurized vessel.

According to embodiments of the present invention, a pressure sealing screw is arranged for discharging hydrothermally treated lignocellulose material from the pressurized vessel.

According to embodiments of the present invention, the discharge chamber is furnished with a mixing device.

According to embodiments of the present invention, the restriction after the discharge chamber has a fixed aperture or has an adjustable aperture.

According to embodiments of the present invention, the restriction is a de Laval nozzle.

According to embodiments of the present invention, steam and vapours after are separated with one or multiple cyclones, or with a centrifuge.

According to embodiments of the present invention, the degassing of reactor is connected to the discharge chamber.

According to embodiments of the present invention, the mixing device is rotating screw.

According to embodiments of the present invention, a mineral acid, for example sulfuric acid, is added to the hydrothermal treatment process up-stream or to the treatment vessel.

BRIEF DESCRIPTION OF THE DRAWINGS

Further objects and advantages of the invention will become apparent from the following description of an apparatus for carrying out the method of the invention shown by way of example in the accompanying figures which form a part of this specification and in which.

DETAILED DESCRIPTION OF THE INVENTION

Figure 1:
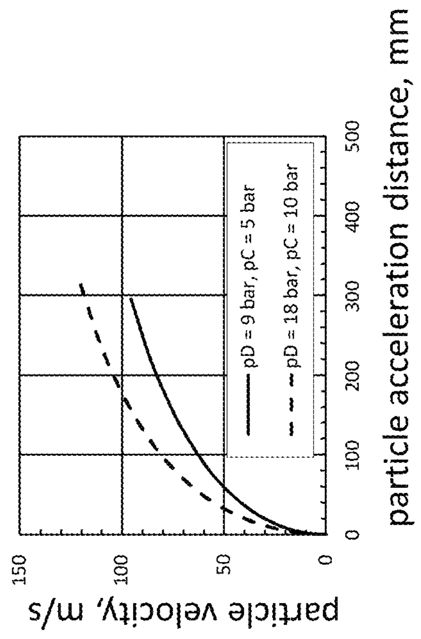
FIG. 1 is a schematic chart illustrating acceleration of wood particles by drag forces caused by pressurized steam at high velocity.

The basic idea behind the invention will now be described with reference to FIGS. 1 and 2. FIG. 1 presents how small biomass particles are accelerated by drag forces when a mixture of steam and lignocellulose particles is released from a compartment at elevated pressure through a fixed discharge opening (orifice or nozzle). At sufficient low back pressure (pressure immediately after discharge nozzle), the pressure will drop to the critical pressure, $p_C$ (critical pressure) in the nozzle. FIG. 1 illustrates the acceleration of biomass particles at the critical pressure conditions prevailing for the steam (motive fluid) in the narrow part of the nozzle. The particle velocities in the figure are given at 18 bar (a) and 9 bar (a) discharge pressures, $p_D$. With discharge pressure $p_D$ is here meant the total pressure at the entrance to the nozzle. The corresponding critical pressures $p_C$ are 9 bar (a) and 5 bar (a) and the steam (motive fluid) velocity at the critical pressures, $p_C$, is approximately 220 m/s in both cases. The particles are accelerated to high velocity at a very short distance. For example, at 100 mm acceleration distance, the velocity is 80 m/s with $p_D$=18 bar (a) pressure to the nozzle and 65 m/s at $p_D$=9 bar (a) pressure to the nozzle. The key observation here is that even though pressure, $p_D$, is reduced 50% the particle velocity is only reduced about 25%. As said above, the particle disintegration, at steam explosion, is heavily affected by impact and wear. Accordingly, it is surprisingly possible to manipulate the pressure before the discharge nozzle without significantly jeopardizing the steam explosion disintegration effect.

Figure 2:
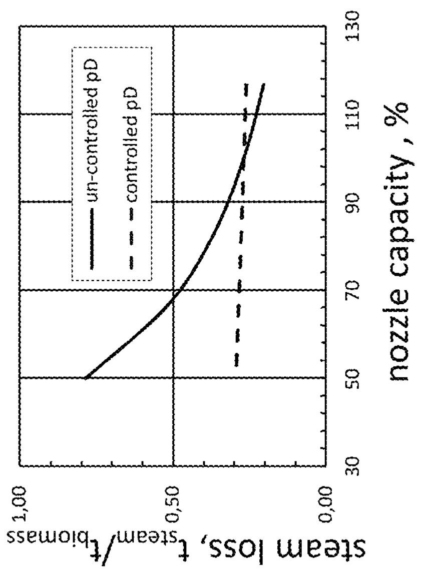
FIG. 2 is schematic chart comparing steam loss at discharge of a conventional reactor with loss at discharge of a reactor according to the present invention.

FIG. 2 presents how the above observations are utilized in the present invention. FIG. 2 is a diagram which presents steam loss with the biomass through a nozzle as a function of nozzle (production) capacity. Steam loss here means the amount of steam which escapes in parallel with biomass at steam explosion discharge through a nozzle. The solid line indicates the steam loss when upstream pressure is kept constant (uncontrolled), for example at 18 bar(a). When the steam explosion discharge is operating at design point for the nozzle 300 kg steam is lost with 1000 kg of biomass. When the production capacity is reduced to 50%, 800 kg steam is lost with 1000 kg of biomass. To avoid such heavy loss of steam (at part load) one may install a control valve in the steam explosion discharge pipe (i.e. prior art) but at the risk of blockage and interrupted production and at the expense of wear on such an expensive control valve. Instead, according to our invention, upstream pressure is controlled, this situation is indicated with the dotted line. The production capacity may vary in the range 50-120% without increasing the steam loss. The steam explosion disintegration effect due to particle velocity and impact remains as demonstrated in FIG. 1.

From above discussion and FIGS. 1 and 2, the inventors have concluded that there is a good basis to propose a steam explosion system with significantly reduced cost of operation, reduced maintenance need and reduced investment costs due to uncomplicated technical design.

Figure 4:
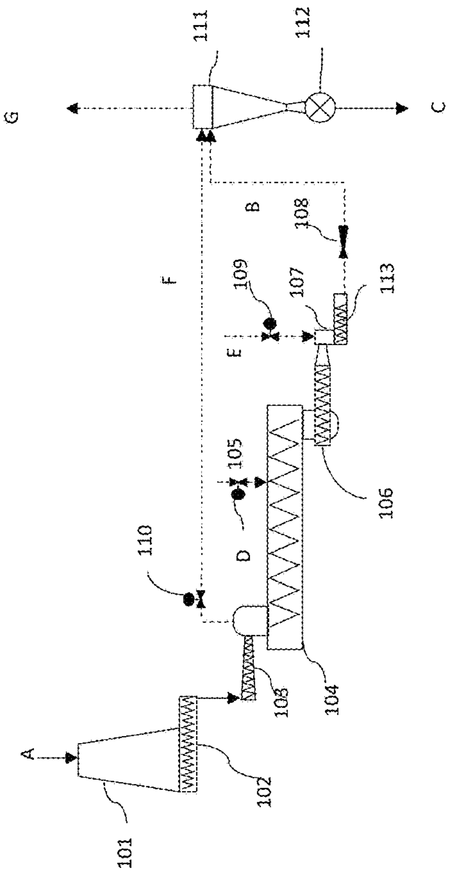
FIG. 4 is yet another schematic illustration of a plant carrying out the method according to embodiments of the present invention.
Figure 3:
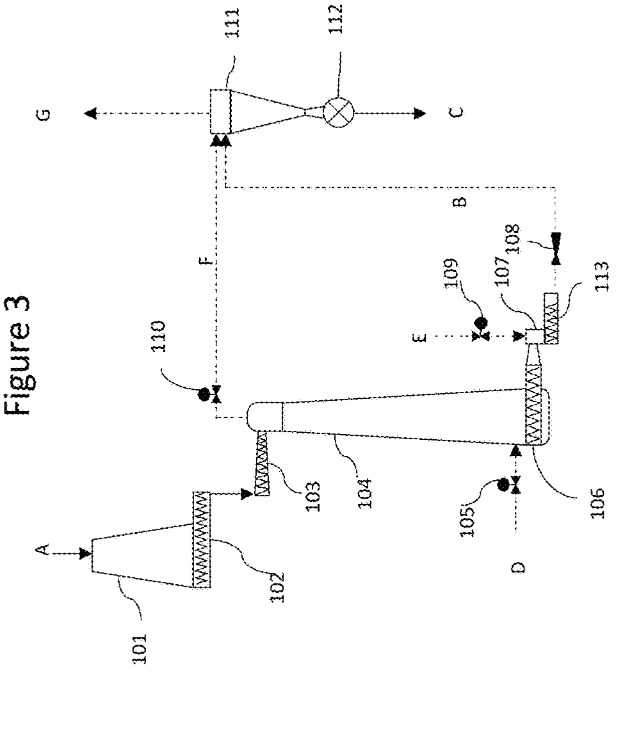
FIG. 3 is a schematic illustration of a plant carrying out the method according to embodiments of the present invention.

Preferred embodiments and their advantages are now described by reference to FIGS. 3 and 4. Referring to the figures, reference numeral 101 denotes a feeding container for biomass. Biomass (A) of woody or agricultural origin, such as wood, bark, bagasse, straw and other, or a mixture thereof is fed to the container. From the container 101 biomass is continuously conveyed with screws or stokers 102, to a conical screw 103 for feeding of it into a pressurized vessel 104, e.g. a reactor. The conical screw compresses the biomass to a gas-tight plug which seals the pressure of the vessel 104 to atmospheric. A conical screw is a preferred but not a mandatory solution of feeding material to the vessel 104. It may optionally be replaced with other technical solutions such as a rotary lock feeder or a lock hopper system. Biomass from the screw 103 falls by gravity inside the vessel 104 and piles up inside the vessel 104. The biomass pile slowly moves downwards as it is continuously emptied in the bottom of the vessel 104 with a discharge screw 106. Biomass inside the vessel 104 is preferably heated counter-currently with condensing steam (D) which is added below the biomass pile. The biomass at the exit, in the discharge screw 106, was heated essentially to the temperature which corresponds to condensing temperature of steam at the pressure prevailing in vessel 104. Hydrolysis of hemicellulose sugars takes place in the heated biomass pile and volatile material such as carboxylic acids, furfural, methanol is released to the gas phase. Accumulation of volatile organic compounds in the gas phase of vessel 104 is avoided by degassing it from the top through a valve 110. The processing condition in reactor vessel 104 is determined essentially by retention time and process temperature and these parameters are controlled by adjusting the biomass (pile) level in the reactor 104 and the reactor pressure with steam supply valve 105. The discharge screw 106 continuously empties the reactor. The discharge screw is like the feeding screw 103 gas-tight which means that no steam passes concurrently with biomass to a discharge chamber 107. The discharge chamber is furnished with an exit conductor including a discharge nozzle 108. The pressure in the discharge chamber 107 is controlled by control valve 109 for supply of steam (E) independently of pressure in vessel 104. The discharge nozzle 108 may comprise an orifice plate, a cylindrical nozzle or a de Laval-nozzle. A de Laval-nozzle is a convergent-divergent special nozzle which in comparison to a cylindrical nozzle converts more expansion work to kinetic energy. This is beneficial as the biomass particles can be accelerated to even higher velocity at a short distance. The discharge nozzle may also be replaced with a valve with an adjustable aperture, but such a valve is not used for control of mass flow of steam from the discharge chamber, such a valve is merely used as a kind of adjustable "fixed" orifice. Biomass from discharge screw 106 enters the discharge chamber 107 which is pressurised with steam (E) through a valve 109 and is discharged through the discharge nozzle 108 as a two-phase flow of steam and biomass particles. As said above, the violent blow and expansion of steam disintegrates the particles when passing the discharge nozzle. The mixture of steam and biomass particles (B) is conveyed to a cyclone 111, for separation of steam and volatile gases (G) from steam exploded material (C). The mixture of volatile gas and steam (F) from the rector 104 is conveyed to the cyclone 111. The cyclone 111 is furnished with a pressure lock at the lower exit to avoid gas passing with biomass to downstream process steps. The pressure lock may, for example, be a rotary lock feeder, 112.

The flow of biomass through the discharge device 107 is controlled by the screws 102, 103 and 106 and the use of steam (E) for steam explosion is determined independently of pressure in the reactor vessel 104. Significant savings in steam usage can be achieved by controlling the pressure in the discharge chamber according to our invention. The particle disintegration during steam explosion can also be controlled independently of the conditions in the reactor vessel 104.

The discharge system may be applied both to a vertically (FIG. 3) and a horizontally (FIG. 4) assembled reactor vessel. The discharging system is not depending on how the feed of biomass to the reactor 104 is arranged (type of biomass container, feed screws and other) or on how steam is separated from biomass after the discharge. The cyclone 111 may for example be replaced with a centrifuge.

The nozzle 108 has a fixed opening and is consequently of a technically uncomplicated design. This means that it can be fabricated from a low cost and very hard, for example ceramic material, thereby lowering costs of maintenance.

Figure 5:
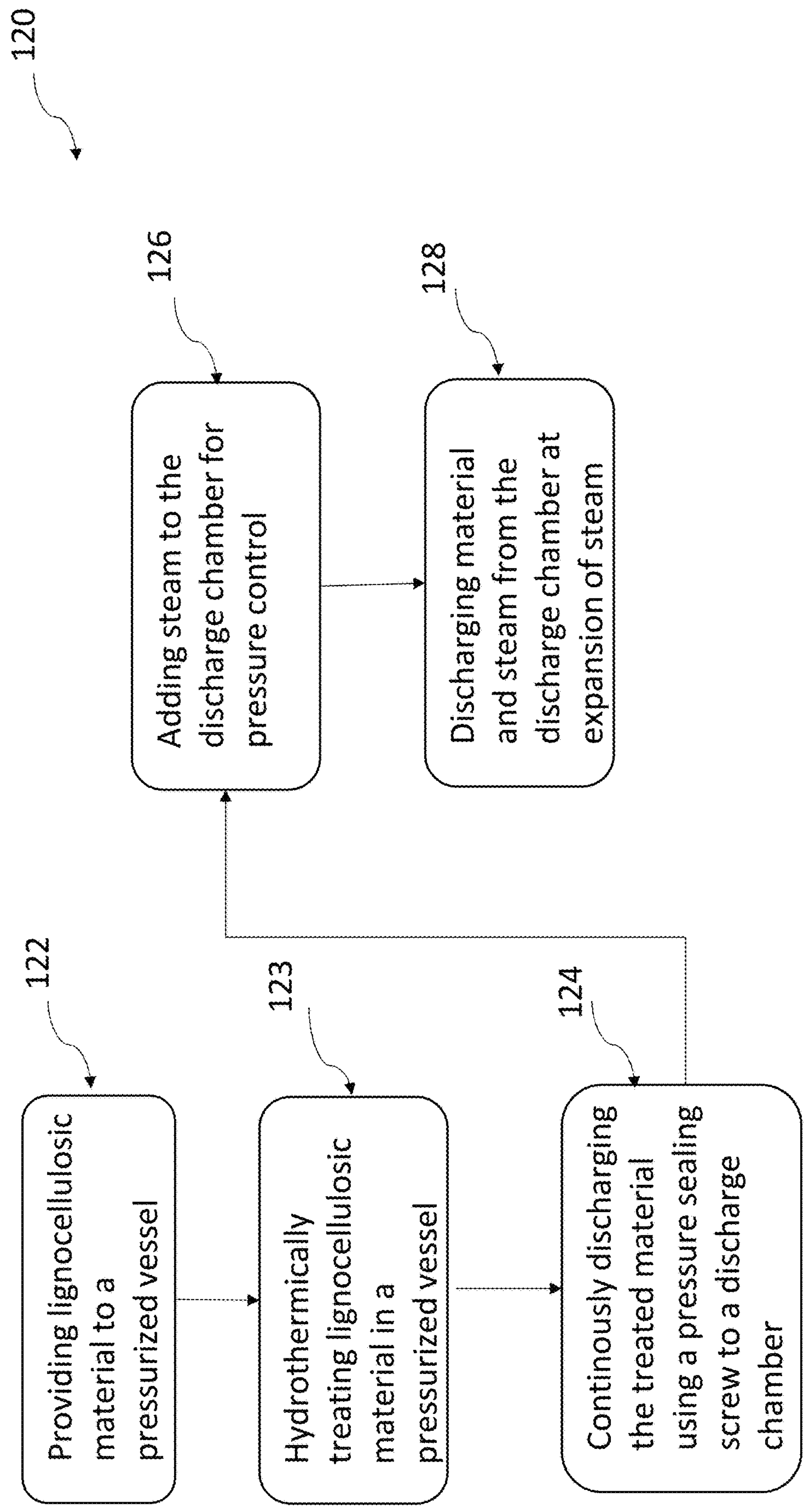
FIG. 5 is a flow chart illustrating a method in accordance to an embodiment of the present invention.

With reference to FIG. 5, an embodiment of a method 120 according to the present invention will be described. First, at step 122, lignocellulosic material to a pressurized vessel 104. Then, at step 123, the lignocellulosic material is hydrothermally treating in the pressurized vessel (104) with saturated or superheated steam. At step 124, the hydrothermally treated lignocellulose material is continuously discharged from a pressurized vessel 104 to a discharge chamber 107 using a pressure sealing screw 106. At step 126, steam E is added to the discharge chamber 107 for pressure control. Thereafter, at step 128, the lignocellulose material and steam is discharged from the discharge chamber 107 through a discharge nozzle 108 at expansion of steam.

The description above and the appended drawings are to be considered as non-limiting examples of the invention. The person skilled in the art realizes that several changes and modifications may be made within the scope of the invention. The discharge chamber 107, may be furnished with multiple steam inlets (E) or multiple discharge conductor with restrictors (B). It may be of vertical or horizontal design, and it may includes a moving device to promote mixing of steam and biomass. The scope of protection is determined by the appended patent claims.

The invention claimed is:

1. A system for processing lignocellulosic materials, the system comprising:

a pressurization vessel configured to perform hydrothermal treatment of the lignocellulosic materials using saturated or superheated steam;

a pressure sealing screw configured to continuously discharge hydrothermally treated lignocellulosic material from the pressurization vessel to a discharge chamber;

a control valve configured to add steam to the discharge chamber for pressure control; and a discharge nozzle configured to discharge the lignocellulosic material and steam from the discharge chamber with expansion of steam;

wherein the control valve is configured to add the steam to the discharge chamber so as to control a pressure in the discharge chamber to different levels at varying flow rates of the lignocellulosic material and to thereby control a ratio of an amount of steam that escapes through the discharge nozzle to an amount of the lignocellulosic material discharged through the discharge nozzle.

2. The system according to claim 1, wherein the pressurization vessel is configured to perform the treatment at a pressure of 5-30 bar (a), and at a temperature of 160-240° C. for a duration of 1-20 minutes.

3. The system according to claim 1, further comprising a mixing device located in the discharge chamber.

4. The system according to claim 3, where the mixing device is rotating screw.

5. The system according to claim 1, where the discharge nozzle comprises a fixed aperture.

6. The system according to claim 1, wherein the discharge nozzle comprises an adjustable aperture.

7. The system according to claim 1, wherein the discharge nozzle is a de Laval nozzle.

8. The system according to claim 1, further comprising a cyclone configured to receive a mixture of steam and biomass particles from the discharge nozzle and to separate the steam and volatile gases from steam exploded material.

9. The system according to claim 1, further comprising a centrifuge configured to receive a mixture of steam and biomass particles from the discharge nozzle and to separate the steam and volatile gases from steam exploded material.

10. The system according to claim 1, further comprising a valve configured to degas the pressurization vessel to the discharge chamber.

* * * * *